(12) United States Patent
Szathmary et al.

(10) Patent No.: US 11,738,084 B2
(45) Date of Patent: Aug. 29, 2023

(54) COMPOSITIONS FOR TRANSFECTION OF BIOMOLECULES INTO CELLS

(76) Inventors: Susan Szathmary, Carlsbad, CA (US); Peter Grandics, Carlsbad, CA (US)

(*) Notice: Subject to any disclaimer, the term of this patent is extended or adjusted under 35 U.S.C. 154(b) by 0 days.

(21) Appl. No.: 13/264,814

(22) PCT Filed: Apr. 19, 2010
(Under 37 CFR 1.47)

(86) PCT No.: PCT/US2010/031559
§ 371 (c)(1),
(2), (4) Date: Apr. 30, 2012

(87) PCT Pub. No.: WO2010/123798
PCT Pub. Date: Oct. 28, 2010

(65) Prior Publication Data
US 2013/0095124 A1    Apr. 18, 2013

Related U.S. Application Data

(60) Provisional application No. 61/170,945, filed on Apr. 20, 2009.

(51) Int. Cl.
*A61K 47/02*   (2006.01)
*A61K 39/02*   (2006.01)
*A61K 39/00*   (2006.01)

(52) U.S. Cl.
CPC .......... *A61K 47/02* (2013.01); *A61K 39/0241* (2013.01); *A61K 2039/552* (2013.01); *A61K 2039/6087* (2013.01); *A61K 2039/62* (2013.01)

(58) Field of Classification Search
CPC ...... A61K 2039/552; A61K 2039/6087; A61K 2039/62; A61K 39/0241; A61K 47/02; A61P 11/06; A61P 29/00; A61P 31/00; A61P 35/00; A61P 35/04; A61P 37/02; A61P 37/06; A61P 37/08; A61P 43/00
USPC ........................................ 424/184.1; 435/375
See application file for complete search history.

(56) References Cited

U.S. PATENT DOCUMENTS

| | | | |
|---|---|---|---|
| 5,684,148 A | 11/1997 | Caruthers et al. | |
| 5,962,674 A | 10/1999 | Iyer et al. | |
| 6,001,982 A | 12/1999 | Ravikumar et al. | |
| 6,031,092 A | 2/2000 | Just et al. | |
| 6,576,271 B2 | 6/2003 | Nair et al. | |
| 7,195,780 B2 * | 3/2007 | Dennis et al. | 424/502 |
| 9,138,467 B2 * | 9/2015 | Szathmary | A61P 37/04 |
| 2002/0061336 A1 * | 5/2002 | O'Connor et al. | 424/499 |
| 2002/0090610 A1 | 7/2002 | Hosken et al. | |
| 2003/0139364 A1 * | 7/2003 | Krieg et al. | 514/44 |
| 2005/0019884 A1 * | 1/2005 | Spector | G01N 33/54353 |
| | | | 435/183 |
| 2007/0281036 A1 * | 12/2007 | Landry et al. | 424/497 |
| 2010/0124754 A1 * | 5/2010 | Wonderling | G01N 33/82 |
| | | | 435/7.1 |
| 2014/0275509 A1 * | 9/2014 | Del Pino Gonzalez de la Higuera | C12Q 1/6811 |
| | | | 536/23.1 |

FOREIGN PATENT DOCUMENTS

| | | | |
|---|---|---|---|
| CN | 101370518 A | 2/2009 | |
| EP | 0350004 A2 * | 1/1990 | G01N 33/579 |
| JP | 4954515 A | 5/1974 | |
| WO | 91/01744 A2 | 2/1991 | |
| WO | WO 1996/039154 A1 | 12/1996 | |
| WO | WO 1997/003211 A1 | 1/1997 | |
| WO | 2004073728 A2 | 9/2004 | |
| WO | 2006/081576 A2 | 8/2006 | |
| WO | WO-2006081576 A2 * | 8/2006 | A61K 39/385 |
| WO | 2007011696 A2 | 1/2007 | |

OTHER PUBLICATIONS

Grolund et al. 2002, Immunology 107, 523-529.*
Fukanaka et al. Journal of Controlled Release vol. 80 Issue 1-3 pp. 333-343, 2002.*
Stamm et al. Nucleic Acids Research Journal, vol. 19, Issue 6, pp. 1350, 1991.*
Burris et al. Environ. Sci. Technol. 1996, 30, 3047-3052. (Year: 1996).*
Shimoni et al. (Journal of the American Oil Chemists' Society vol. 71, pp. 641-644 (1994) (Year: 1994).*
Office Action for Corresponding Chinese Patent Application No. 201080027552.1, dated Sep. 17, 2013.
W. Samstag et al., "Synthesis and Properties of New Antisense Oligonucleotides Containing Benzylphosphonate Linkages," Antisense Nucl. Acid. Drug Develop. 6: 153-156 (1996).
H. Gronlund et al., "Carbohydrate-Based Particles: A New Adjuvant for Allergen-Specific Immunotherapy," Immunology 107: 523-529 (2002).
D.J. Brayden, "Oral Vaccination in Man Using Antigens in Particles: Current Status," Eur. J. Pharmaceut. Sci. 14: 183-189 (2001).

* cited by examiner

*Primary Examiner* — Janet L Epps-Smith
(74) *Attorney, Agent, or Firm* — Ditthavong, Steiner & Mlotkowski

(57) ABSTRACT

The present invention is directed to new compositions that are described for the simultaneous, controlled dose delivery of a variety of biomolecules into phagocytic cells. Such a composition is a biologically active composition comprising: (1) at least one of the following biologically active components: (a) a nucleic acid or a derivative thereof; (b) a nucleoside, nucleotide, or a derivative of a nucleoside or nucleotide; (c) a peptide, protein, or a derivative of a peptide or protein; (d) a lipopolysaccharide or a derivative thereof; (e) a peptidoglycan or a derivative thereof; (f) a carbohydrate or a derivative thereof; (g) a lipid or a derivative thereof; (h) a lipopeptide or a derivative thereof; (i) a metal ion; (j) a thiol; (k) an antibiotic or a derivative thereof; (l) a vitamin or a derivative thereof; (m) a bioflavonoid or a derivative thereof; (n) an antioxidant or a derivative thereof; (o) an immune response modifier; (p) an antibody; (q) a biologically active nonmetal; (r) histamine or an antihistamine; and (s) a kinase inhibitor; and (2) at least one carrier effective to deliver the composition to a phagocytic cell such that the biologically active component is taken up by the phagocytic cell and influences its biological activity.

11 Claims, No Drawings

COMPOSITIONS FOR TRANSFECTION OF BIOMOLECULES INTO CELLS

CROSS-REFERENCES

This PCT application claims priority from U.S. Provisional Application Ser. No. 61/170,945 by Grandics et al., entitled "Compositions for Transfection of Biomolecules into Cells," and filed on Apr. 20, 2009, the contents of which are hereby incorporated herein in their entirety by this reference.

BACKGROUND OF THE INVENTION

This invention provides compositions that can introduce (transfect) biologically active molecules into mammalian cells. Transfection of nucleic acids is a well-developed area of molecular biology utilizing a variety of methods like reagents (e.g., DEAE-dextran, calcium phosphate, lipofectin, viral vectors), electroporation, gene guns or microinjection. Protein delivery methods also include cationic lipids, liposomes and carrier peptides. Transfection of carbohydrates is not well developed along with the controlled dose introduction of specific metals. In addition, it would be important to develop a transfection method that allowed a controlled dose, simultaneous delivery of numerous biologically active components (nucleic acids and derivatives, lipopeptides, lipopolysaccharides, peptidoglycans, lipids, proteins and peptides, ions, thiol compounds, antibiotics, vitamins, bioflavonoids, antioxidants, etc.) into specific cell subsets like phagocytic cells, including dendritic cells, macrophages and B cells. The widely different physicochemical characteristics of these molecules can lead to interference in their incorporation into current delivery vehicles that target nonspecifically a wide range of cell types in vivo. Therefore, there is a need for a new cell delivery system that works both in vitro and in vivo for the simultaneous transfection of the possibly widest range of biomolecules into phagocytic cells.

SUMMARY OF THE INVENTION

Pursuant to this invention, new compositions are described for the simultaneous, controlled dose delivery of a variety of biomolecules into phagocytic cells.

Accordingly, one aspect of the present invention is a biologically active composition comprising:
(1) at least one of the following biologically active components:
  (a) a nucleic acid or a derivative thereof;
  (b) a nucleoside, nucleotide, or a derivative of a nucleoside or nucleotide;
  (c) a peptide, protein, or a derivative of a peptide or protein;
  (d) a lipopolysaccharide or a derivative thereof;
  (e) a peptidoglycan or a derivative thereof;
  (f) a carbohydrate or a derivative thereof;
  (g) a lipid or a derivative thereof;
  (h) a lipopeptide or a derivative thereof;
  (i) a metal ion;
  (j) a thiol;
  (k) an antibiotic or a derivative thereof;
  (l) a vitamin or a derivative thereof;
  (m) a bioflavonoid or a derivative thereof;
  (n) an antioxidant or a derivative thereof;
  (o) an immune response modifier;
  (p) an antibody;
  (q) a biologically active nonmetal;
  (r) histamine or an antihistamine; and
  (s) a kinase inhibitor; and
(2) at least one carrier effective to deliver the composition to a phagocytic cell such that the biologically active component is taken up by the phagocytic cell and influences its biological activity.

In the compositions, the molecules can be present as a mixture. Alternatively, the molecules can be chemically linked together. The carrier is typically a microparticle. Preferably, the microparticles have a narrow size distribution range. The microparticles can be porous or non-porous. Typically, the microparticles are less than about 10 µm in diameter; more typically, the microparticles are less than about 5 µm in diameter. Typically, the microparticles are made of a biopolymer. In one alternative, the components are noncovalently attached to the microparticles. In another alternative, the components are covalently attached to the microparticles.

Another aspect of the present invention is a method of eliciting a biological response in a cell culture or cell subset or in a multicellular organism such as a plant, an animal, or a human subject comprising the step of administering an effective amount of a composition comprising the selected biologically active component associated with microparticles, wherein the microparticles are smaller than or in the same size range as a pathogen.

According to the present invention, administration of the composition can be performed in a cell culture or via a mucosal route, a parenteral route, or a dermal route into a host. Other routes of administration could alternatively be used.

Another aspect of the present invention is a method for studying the effect of acute infections, a chronic inflammatory disease selected from the group consisting of allergies, asthma, autoimmune conditions, and cancer, or tumor metastasis comprising the steps of:
(1) providing an animal model susceptible to a condition selected from the group consisting of allergies, asthma, autoimmune conditions, cancer, and tumor metastasis;
(2) administering a composition according to the present invention, wherein, in the composition, the microparticles are in the same size range as a pathogen, wherein the composition comprises an immune active antigen or antigenic epitope, and wherein the immune active antigen or antigenic epitope is a peptide, a protein, a recombinant peptide or multi-peptide, or a recombinant protein, to the animal model to treat or prevent an infection in the animal model through an immune response resulting from the administration of the composition; and
(3) determining the effect of the composition administered in step (2) on the condition selected from the group consisting of allergies, asthma, autoimmune conditions, cancer, and tumor metastasis.

DESCRIPTION OF THE PREFERRED EMBODIMENT

This invention describes compositions and methods of targeting such compositions to certain cell populations and eliciting an immunological response in an animal model.

There is a need to produce agents and delivery vehicles for the controlled dose delivery of multiple biologically active molecules that have mutually exclusive physicochemical characteristics. For instance, nucleic acids or lipopolysaccharides precipitate out in the presence of polyamine molecules, basic peptides and/or transitional metals (e.g., Zn ions), a phenomenon that precludes their mixing and simultaneous administration with other biologically active molecules even though their controlled dose administration to cells would be necessary for evoking specific physiological responses (e.g., protective immunity). Cationic lipid/liposome delivery vehicles are not effective for the delivery of cationic molecules. We reasoned that a pathogen-sized microparticle would provide an optimal method for the delivery of biomolecules (also described herein as biologically active components) of vastly different physicochemical properties as selective, consecutive attachment of ligands is possible. Thus, targeted dosing of biologically active molecules to large numbers of phagocytic cells could be carried out by this invention.

We have investigated the targeting of biologically active molecules to specific cells by a carrier comprised of a polysaccharide, such as native agarose or other biodegradable carriers. Agarose has the advantage that it is a natural polysaccharide, a D-galactose polymer that is biodegradable and proven compatible with mammalian cells. Parenterally administered agarose micro-particles have been found to exhibit weak macrophage activating capacity and a comparable adjuvant property to aluminum hydroxide (Gronlund H. et al., Carbohydrate-based particles: a new adjuvant for allergen-specific immunotherapy. Immunology, 2002; 107, 523-529).

From an end-user point of view, it is important that the composition requires no refrigerated storage and still has a long shelf life. Agarose particles meet these requirements. Also, it is important that the administration of the composition be as simple as possible. Therefore, a mucosally administrable composition has advantages over parenterals. Mucosal applications, however, have been plagued with stability problems due to the catabolic effects of the digestive system.

We have reasoned that biomolecules coupled to the porous agarose matrix might be protected from degradation inside the GI tract. Also, the size of the agarose microparticles (<5 μm) may make them suitable for allowing the particles to pass into the Peyer's patches (PP).

We have established in an animal model system that a significant degree of immune protection can be achieved against the infectious strain of *Mycoplasma gallisepticum* when the animals were administered the composition of the present invention prior to mycoplasmal challenge. In addition, the reversal of characteristic pathological symptoms was also observed on pre-infected animals indicating that such microparticles were effective to treat an infected animal. This is significant because of the widespread antibiotic resistance of various strains of microorganisms. In addition, we have found that just a very small amount of antigen (1-10 μg) per animal was necessary to elicit a protective response by this method as opposed to over 100 μg described in the literature using microparticles that had incorporated the antigen. (Brayden, D. 2001 European Journal of Pharmaceutical Sciences 14:183-189). This suggests that the immune modulator particle(s) are not degraded while traversing the gut in the animals and that it is delivered to the targeted mucosal immune cells in an efficacious manner.

The bioactive molecules can be non-covalently or covalently attached to the microparticles. Methods for covalent attachment are known in the art and are described for example, in P. Tijssen, "Practice and Theory of Enzyme Immunoassays" (Elsevier, Amsterdam, 1985, pp. 283-289, in S. S. Wong, "Chemistry of Protein Conjugation and Crosslinking" (CRC Press, Boca Raton, Fla., 1993), in T. E. Creighton, ed., "Protein Function: A Practical Approach" (IRL Press, Oxford, 1989), and in G. T. Hermanson, "Bioconjugate Techniques" (Academic Press, San Diego, 1996), all of which are incorporated herein by this reference. Typically, when the microparticles are biodegradable natural polysaccharides such as agarose, the bioactive molecule is attached to a hydroxyl group of the polymeric chains of the biodegradable natural polysaccharide. In general, certain compounds that form intermediate reactive derivatives containing good leaving groups for subsequent nucleophilic substitution can activate the hydroxyl residues of polysaccharides. Reaction of these activated hydroxyls with nucleophiles such as amines (for example, lysine groups in proteins or peptides) results in stable covalent bonds that crosslink the bioactive molecule to the polymeric chains of the biodegradable natural polysaccharide. Suitable reagents include carbonyldiimidazole, chloroformate derivatives, tresyl chloride, tosyl chloride, cyanogen bromide, divinylsulfone, cyanuric chloride, and bis-epoxides. Alternatively, the hydroxyl groups of carbohydrate polymers such as agarose can be modified with chloroacetic acid to create a carboxylate functional group. As another alternative, amine functional groups can be created on polysaccharides; the reducing ends of carbohydrate molecules or generated aldehydes can be reacted with diamine compounds of low chain length (i.e., typically less than about 6 carbon atoms in the chain) to yield short alkylamine spacers that can be used for subsequent conjugation reactions. Hydrazide groups can be similarly created using bis-hydrazide compounds. The resulting functional group can then be coupled to the bioactive molecule using various reactions. For example, if carboxyl groups are generated, they can then be conjugated to proteins or peptides via the mixed anhydride method, the carbodiimide method, using dicyclohexylcarbodiimide, or the N-hydroxysuccinimide ester method. Aliphatic amines can be conjugated to proteins or peptides by various methods, including carbodiimide, tolylene-2,4-diisocyanate, or malemide compounds, particularly the N-hydroxysuccinimide esters of malemide derivatives. An example of such a compound is 4-(N-maleimidomethyl)-cyclohexane-1-carboxylic acid. Another example is m-maleimidobenzoyl-N-hydroxysuccinimide ester. Still another reagent that can be used is N-succinimidyl-3-(2-pyridyldithio)propionate. Also, bifunctional esters, such as dimethylpimelimidate, dimethyladipimidate, or dimethylsuberimidate, can be used to couple amino group containing moieties to proteins. Other methods for covalent linkage of compounds, including peptides, proteins, and carbohydrates, as well as other compounds, to solid supports are known in the art. Methods for noncovalent attachment depend on multiple noncovalent interactions such as hydrogen bonds, hydrophobic bonds, metal chelate and salt linkages that can stabilize the interaction.

Typically, the biomolecule to be delivered (also described herein as a biologically active component), is at least one of the following:

(1) a nucleic acid or a derivative thereof;
(2) a nucleoside, nucleotide, or a derivative of a nucleoside or nucleotide;
(3) a peptide, protein, or a derivative of a peptide or protein;
(4) a lipopolysaccharide or a derivative thereof;
(5) a peptidoglycan or a derivative thereof;
(6) a carbohydrate or a derivative thereof;
(7) a lipid or a derivative thereof;
(8) a lipopeptide or a derivative thereof;
(9) a metal ion;
(10) a thiol;
(11) an antibiotic or a derivative thereof;

(12) a vitamin or a derivative thereof;
(13) a bioflavonoid or a derivative thereof;
(14) an antioxidant or a derivative thereof;
(15) an immune response modifier;
(16) an antibody;
(17) a biologically active nonmetal;
(18) histamine or an antihistamine; and
(19) a kinase inhibitor.

As used herein, the term "nucleic acid" refers to a deoxyribonucleotide or ribonucleotide oligonucleotide or polynucleotide, including single- or double-stranded forms, and coding or non-coding (e.g., "antisense") forms. The term encompasses nucleic acids containing known analogues of natural nucleotides. The term also encompasses nucleic acids including modified or substituted bases as long as the modified or substituted bases interfere neither with the Watson-Crick binding of complementary nucleotides or with the binding of the nucleotide sequence by proteins that bind specifically, such as zinc finger proteins. The term also encompasses nucleic-acid-like structures with synthetic backbones. DNA backbone analogues provided by the invention include phosphodiester, phosphorothioate, phosphorodithionate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS1992); Milligan (1993) J. Med. Chem. 36:1923-1937; Antisense Research and Applications (1993, CRC Press). PNAs contain non-ionic backbones, such as N-(2-aminoethyl)glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189-197. Other synthetic backbones encompassed by the term include methylphosphonate linkages or alternating methylphosphonate and phosphodiester linkages (see, e.g., U.S. Pat. No. 5,962,674; Strauss-Soukup (1997) Biochemistry 36:8692-8698), and benzylphosphonate linkages (see, e.g., U.S. Pat. No. 5,532,226; Samstag (1996) Antisense Nucleic Acid Drug (Dev 6:153-156).

As used herein, the term "nucleic acid" also includes both DNA and RNA, as well as both naturally occurring and synthetic forms of both DNA and RNA, as well as RNA-DNA hybrids. Regarding DNA, the term "nucleic acid" encompasses both single-stranded and double-stranded DNA, as well as partially double-stranded DNA; it further encompasses both linear and circular DNA as well as cDNA prepared by the reverse transcription of messenger RNA (mRNA). Regarding RNA, the term "nucleic acid" encompasses forms of RNA such as ribosomal RNA (rRNA), transfer RNA (tRNA), and messenger RNA (mRNA), as well as RNA molecules such as small interfering RNA (siRNA), which are short double-stranded RNA molecules that are 20-25 nucleotides in length that have 2-nucleotide 3' overhangs on either end that are active in the RNA interference pathway, interfering with the expression of a specific gene, and small hairpin RNAs. Another example of a class of nucleic acids that can be incorporated into the present invention is micro RNAs. These are noncoding oligonucleotides that are potent regulators of gene expression that play a pivotal role in shaping cellular development and differentiation in various tissues. Dysregulated micro RNA levels are associated with various malignancies. Another type of nucleic acids that can be incorporated into the present invention is poly I:C (Example 4), which is an immunostimulant that known to interact with Toll-like receptor (TLR) 3, which is expressed in the intracellular compartments of B-cells and dendritic cells. Poly I:C is structurally similar to double-stranded RNA, which is present in some viruses and is a "natural" stimulant of TLR3. Thus, Poly I:C can be considered a synthetic analogue of double-stranded RNA. Toll-like receptors 7, 8, and 9 are all involved in sensing pathogen-derived nucleic acids or oligonucleotides.

Many nucleotides and nucleosides are known to be biologically active. Examples include, but are not limited to, adenosine triphosphate (ATP), guanosine triphosphate (GTP) and cyclic AMP (cAMP). ATP and GTP are energy sources, while CAMP acts as a signaling modulator or second messenger in many signal transduction systems. Other biologically active nucleotides and nucleosides are known in the art.

Proteins include enzymes, membrane proteins, secreted proteins, transport proteins, receptor proteins, structural proteins, antibodies, antibody fragments, and other biologically active proteins. As used herein, the term "protein" encompasses both proteins comprising a single polypeptide chain and proteins comprising multiple polypeptide chains, sometimes referred to as "subunits," when a protein comprises subunits, the subunits can be held together by covalent or non-covalent interactions. Reference herein to "proteins" includes reference to individual subunits of a multi-subunit protein. Peptides are poly-α-amino acid chains of less than about 50 amino acids in length; longer chains of poly-α-amino acids are generally classified as proteins or subunits of proteins. Many peptides are biologically active; examples include, but are not limited to, thymulin, tachykinin peptides such as Substance P and Neurokinin A and B, vasoactive intestinal peptide, enkephalin peptides, antimicrobial basic peptides, angiotensin, proline-rich peptides, calcitonin, amylin, glucagon, and secretin. Other peptides with biological activity that can be incorporated into compositions according to the present invention include, but are not limited to, polybasic peptides such as polylysine and antimicrobial basic peptides, as well as peptide epitopes and mixtures of peptide epitopes such as the MHC I and MHC II peptide epitope mixture (G1/9+G2/4) (Example 4) or peptide B3 (Examples 8-10). Many others are known in the art. Also within the scope of biologically active proteins or peptides that can be included in compositions according to the present invention are recombinant proteins, recombinant peptides, and multi-peptides. Additionally within the scope of biologically active proteins that can be included in compositions according to the present invention are monoclonal antibodies that act as protein kinase inhibitors, such as, but not limited to, bevacizumab targeting the phosphorylation of VEGF, cetuximab targeting the phosphorylation of Erb1, trastuzumab targeting the phosphorylation of Erb2, ranibzumab targeting the phosphorylation of VEGF, and panitumumab targeting the phosphorylation of EGFR. Inhibitors of mTOR can also be included in the compositions to regulate cell proliferation, metabolism, and angiogenesis. The protein mTOR (mammalian target of rapamycin) is also known as FK506 binding protein 12-rapamycin associated protein 1 (FRAP1). It is a serine/threonine protein kinase that regulates cell growth, cell proliferation, cell motility, cell survival, protein synthesis, and transcription. Inhibitors of mTOR include rapamycin, FK506 (tacrolimus), and analogues and derivatives thereof.

Lipopolysaccharides, also known as lipoglycans, are large molecules consisting of a lipid and a polysaccharide joined by covalent bonds. They are located in the outer membrane of Gram-negative bacteria; they act as endotoxins and elicit strong immune responses. Lipopolysaccharides comprise three components: (1) polysaccharide (O) side chains; (2) core polysaccharide (core oligosaccharide in some species); and (3) Lipid A. Lipopolysaccharides can be modified to present a specific structure.

Peptidoglycans are polymers consisting of sugars and amino acids that forms a mesh-like layer outside the plasma membrane of bacteria, forming the cell wall. The sugar component consists of alternating residues of β-(1,4) linked N-acetylglucosamine and N-acetylmuramic acid residues. Attached to the N-acetylmuramic acid is a peptide chain of three to five amino acids. The peptide chain can be cross-linked to the peptide chain of another strand forming the 3D mesh-like layer. The peptidoglycan layer in the bacterial cell wall is a crystal lattice structure formed from linear chains of two alternating amino sugars, namely N-acetylglucosamine (GlcNAc or NAG) and N-acetylmuramic acid (MurNAc or NAM). The alternating sugars are connected by a β-(1,4)-glycosidic linkage. Each MurNAc is attached to a short (4- to 5-residue) amino acid chain, containing D-alanine, D-glutamic acid, and meso-diaminopimelic acid in the case of *Escherichia coli* (a Gram negative) or L-alanine, D-glutamine, L-lysine, and D-alanine in the case of *Staphylococcus aureus* (a Gram positive bacterium). These amino acids, except the L-amino acids, do not occur in proteins and are thought to help protect against attacks by most peptidases. Cross-linking between amino acids in different linear amino sugar chains by an enzyme known as transpeptidase result in a 3-dimensional structure that is strong and rigid. The specific amino acid sequence and molecular structure vary with the bacterial species.

Carbohydrates include monosaccharides, oligosaccharides, and polysaccharides. Polysaccharides can include heteropolysaccharides and homopolysaccharides; they include both branched and linear polymers. Many carbohydrates are important components of receptors and other molecules involved in immune response and signal transduction.

Lipids include fatty acids, triacylglycerols, glycerophospholipids such as phosphatidic acid, phosphatidylethanolamine, phosphatidylserine, phosphatidylcholine, phosphatidylinositol, phosphatidylglycerol, and diphosphatidylglycerol, ceramide, sphingolipids such as sphingomyelins and cerebrosides, and sterols such as cholesterol. Lipids are important components of cell membranes and play key roles in maintaining the structure of cell membranes and regulating their permeability to solutes. They also participate in inducing and regulating the immune response.

Lipopeptides are molecules consisting of a lipid covalently bound to a peptide. They are expressed by bacteria and are specifically bound by TLR1 and other Toll-like receptors. Examples include, but are not limited to, surfactin and daptomycin. Lipopeptides are described in U.S. Pat. No. 6,911,525 to Hill et al., incorporated herein in its entirety by this reference.

Metal ions, such as $Zn^{2+}$, $Cu^{2+}$, $Fe^{2+}$, $Fe^{3+}$, and $Mn^{2+}$ are frequently involved in enzymatic reactions as cofactors. Additionally, positively-charged metal ions can bind negatively-charged nucleic acids as part of zinc finger proteins, and positively-charged metal ions, especially $Fe^{2+}$, also are part of oxygen transport proteins such as myoglobin and hemoglobin.

Thiols are biological reductants and participate in a number of biologically significant redox processes, such as reducing disulfide bonds in proteins to convert the oxidized cysteine residues to their reduced form. Examples of biologically active thiol molecules are glutathione and N-acetylcysteine, both playing an important role in the immune response.

Antibiotics are molecules, typically produced or derived from bacteria or fungi, that kill or block the growth of undesirable microbes. Many antibiotics are known in the art; for example, the antibiotic can be, but is not limited to, ofloxacin, tiamulin, tetracyclines, erythromycin, penicillins, methicillin, nafcillin, oxacillin, cloxacillin, dicloxacillin, ampicillin, amoxicillin, bacampicillin, carbenicillin, ticarcillin, mezlocillin, piperacillin, cephalosporins, gentamicin, tobramycin, amikacin, netilmycin, kanamycin, neomycin, clarithromycin, azithromycin, clindamycin, spectinomycin, vancomycin, and rifamycins. The use of other antibiotics is possible. The structures and uses of these and other antibiotics are disclosed in J. G. Hardman & L. G. Limbird, eds., Goodman & Gilman's The Pharmacological Basis of Therapeutics (9th ed., McGraw-Hill, New York, 1996), pp. 1073-1153, incorporated herein by this reference. In addition, certain proteins or derivatives of proteins have antibacterial activity and are included with the definition of "antibiotics" as used herein. These include lactoferrin and lactoferricin. Besides their antimicrobial effects, antibiotics also affect both innate and adaptive immune responses.

Vitamins typically act as coenzymes or cofactors in biochemical reactions. Vitamins include vitamin A (retinoids), vitamin B, (thiamine), vitamin $B_2$ (riboflavin), vitamin $B_3$ (niacin or niacinamide), vitamin $B_6$ (pyridoxal phosphate, pyridoxamine), vitamin $B_7$ (biotin), vitamin $B_9$ (folic acid), vitamin $B_{12}$ (cyanocobalamin), vitamin C (ascorbic acid), vitamin D (ergocalciferol or cholecalciferol), vitamin E (tocopherols and tocotrienols), and vitamin K (phylloquinone and menaquinones). Vitamins can also directly influence the immune response.

Bioflavonoids are biological antioxidants and, among other functions, prevent or retard damage caused in biological systems by free radicals. For example, the bioflavonoid can be, but is not limited to, quercetin, quercitrin, kaempferol, kaempferol 3-rutinoside, 3'-methoxy kaempferol 3-rutinoside, 5,8,4'-trihydroxyl-6,7-dimethoxyflavone, catechin, epicachetin, epicachetin gallate, epigallocachetin gallate, hesperidin, naringin, rutin, vixetin, proanthocyanidin, apigenin, myricetin, tricetin, quercetin, naringin, kaempferol, luteolin, biflavonyl, silybin, silydianin, and silychristin, or derivatives and glycosides of these compounds. Bioflavonoids are described, for example, in U.S. Pat. No. 6,576,271 to Nair et al., incorporated herein by this reference.

Biological antioxidants have the property of inhibiting, slowing, retarding, or preventing biological oxidation reactions, which can oxidize proteins, nucleic acids, carbohydrates, or lipids and thus contribute to cellular damage. These biological antioxidants typically operate by preventing damage caused by reactive oxygen species such as include hydrogen peroxide ($H_2O_2$), hypochlorous acid (HOCl), and free radicals such as the hydroxyl radical (·OH) and the superoxide anion ($O_2^-$). Such biological antioxidants include thiols such as glutathione, described above, vitamins such as vitamin A, vitamin C, and vitamin E, as well as curcumin, uric acid, lipoic acid, carotenes, and ubiquinol (coenzyme Q). Others are known in the art.

Immune response modifiers activate the immune system. An example is imiquimod. Imiquimod activates immune cells through the toll-like receptor 7 (TLR7), commonly involved in pathogen recognition, on the cell surface. Cells activated by imiquimod via TLR-7 secrete cytokines (primarily interferon-α (IFN-α), interleukin-6 (IL-6) and tumor necrosis factor-α (TNF-α)). There is evidence that imiquimod, when applied to skin, can lead to the activation of Langerhans cells, which subsequently migrates to local lymph nodes to activate the adaptive immune system. Other cell types activated by imiquimod include natural killer cells, macrophages and B-lymphocytes. New research has shown that imiquimod's anti-proliferative effect is exerted by increasing levels of the opioid growth factor receptor (OGFr). Blocking OGFr function with siRNA technology resulted in loss of any antiproliferative effect of imiquimod.

The structure and activity of antibodies are well known in the art. Antibodies specifically bind their corresponding antigens through complementary noncovalent interactions. Antibodies belong to the general class of serum glycoproteins called immunoglobulins, which are made in all vertebrates as part of the immune response to antigenic challenge by substances recognized by the immune system as foreign. Naturally occurring antibodies are Y-shaped proteins made up of two identical heavy (H) chains, each with a molecular weight of about 50 kDa, and two identical light (L) chains, each with a molecular weight of about 25 kDa, held together by disulfide bonds. Each naturally occurring antibody has two antigen binding sites, formed by particular portions of both the heavy and light chains, designated as the variable regions, more specifically as the hypervariable regions within the variable regions. The specific binding of antigens to antibody molecules activates a number of biological functions through portions of the heavy and light chains, designated as the constant regions, that are distinct from the variable regions. These biological functions include complement activation, opsonization of pathogens, and activation of a number of cell types.

The preparation of such antibodies is well known in the art and need not be described further herein. In general, antibodies according to the present invention can be of any class, such as IgG, IgA, IgD, IgE, IgM, or IgY, although IgG antibodies are typically preferred. Antibodies can be of any mammalian or avian origin, including human, murine (mouse or rat), donkey, sheep, goat, rabbit, camel, horse, or chicken. In some alternatives, the antibodies can be bispecific. The antibodies can be modified by the covalent attachment of any type of molecule to the antibody. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, or other modifications known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., "Antibodies: A Laboratory Manual", (Cold Spring Harbor Laboratory Press, 2nd ed. 1988); Hammerling, et al., in: Monoclonal Antibodies and T-Cell Hybridomas 563-681 (Elsevier, N.Y., 1981), or by other standard methods known in the art. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. For example, suitable antibodies can be produced by phage display or other techniques. Additionally, and not by way of limitation, human antibodies can be made by a variety of techniques, including phage display methods using antibody libraries derived from human immunoglobulin sequences and by the use of transgenic mice that are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. The antibodies can also be produced by expression of polynucleotides encoding these antibodies. Additionally, antibodies according to the present invention can be fused to marker sequences, such as a peptide tag to facilitate purification; a suitable tag is a hexahistidine tag. The antibodies can also be conjugated to a diagnostic or therapeutic agent by methods known in the art. Techniques for preparing such conjugates are well known in the art.

Other methods of preparing these monoclonal antibodies, as well as chimeric antibodies, humanized antibodies, and single-chain antibodies, are known in the art. In some cases, human monoclonal antibodies are suitable for use in compositions and can be prepared by a number of methods known in the art, including phage display techniques and mice genetically engineered to produce human antibodies.

As used herein, unless otherwise specifically limited, the term "antibody" includes all types of antibodies described herein, including, but not limited to, naturally occurring antibodies, monoclonal antibodies, genetically engineered antibodies, single-chain antibodies, derivatized antibodies, chimeric antibodies, humanized antibodies, human antibodies, and other types of antibodies.

Biologically active nonmetals include selenium, which is an essential micronutrient and a component of the unusual amino acids selenocysteine and selenomethionine. In humans, selenium is a trace element nutrient which functions as cofactor for reduction of antioxidant enzymes such as glutathione peroxidases and certain forms of thioredoxin reductase found in animals and some plants.

Histamine is the decarboxylation product of histidine. Histamine acts on at least four distinct receptors, $H_1$ receptors, $H_2$ receptors, $H_3$ receptors, and $H_4$ receptors. It increases vascular permeability and is a mediator of inflammatory reactions through that and other effects. Antihistamines are widely used to treat a variety of inflammatory conditions, including allergies. Antihistamines include, but are not limited to, doxepin hydrochloride, carbinoxamine maleate, clemastine fumarate, diphenhydramine hydrochloride, dimenhydrinate, pyrilamine citrate, tripelennamine hydrochloride, tripelennamine citrate, chlorpheniramine maleate, brompheniramine maleate, hydroxyzine hydrochloride, hydroxyzine pamoate, cyclizine hydrochloride, cyclizine lactate, meclizine hydrochloride, promethazine hydrochloride, cyproheptadine hydrochloride, phenindamine tartrate, acrivastine, cetirizine hydrochloride, azelastine hydrochloride, levocabastine hydrochloride, loratidine, desloratidine, ebastine, mizolastine, and fexofenadine, and the salts, solvates, analogues, congeners, bioisosteres, hydrolysis products, metabolites, precursors, and prodrugs thereof.

Kinase inhibitors inhibit phosphorylation of serine, tyrosine, threonine, or, in some cases, histidine residues of proteins. Kinase inhibitors include small molecule kinase inhibitors. Examples of such small molecule kinase inhibitors include, but are not limited to, BIBW 2992, which inhibits EGFR and Her2/neu, and has the chemical structure N-[4-[(3-chloro-4-fluorophenyl)amino]-7-[[(3S)-tetrahydro-3-furanyl]oxy]-6-quinazolinyl]-4(dimethylamino)-2-butenamide, imatinib (Gleevec), which inhibits tyrosine kinase enzymes and has the chemical structure 4-[(4-methylpiperazin-1-yl)methyl]-N-[4-methyl-3-[(4-pyridin-3-ylpyrimidin-2-yl)amino]phenyl]benzamide, gefinitib, which inhibits EGFR's tyrosine kinase domain and has the chemical structure N-(3-chloro-4-fluoro-phenyl)-7-methoxy-6-(3-morpholin-4-ylpropoxy)quinazolin-4-amine, pegaptanib, which inhibits VEGF, sorafenib, which inhibits several protein kinases and has the chemical structure 4-[4-[[4-chloro-3-(trifluoromethyl)phenyl]carbamoylamino]phenoxy]-N-methyl-pyridine-2-carboxamide, dasatinib, which also inhibits several protein kinases and has the chemical structure N-(2-chloro-6-methylphenyl)-2-[[6-[4-(2-hydroxyethyl)-1-piperazinyl]-2-methyl-4-pyrimidinyl]amino]-5-thiazolecarboxamide monohydrate, sunitinib, which inhibits several receptor protein kinases and has the chemical structure N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, erlotinib, which inhibits EGFR tyrosine kinase and has the chemical structure N-(3-ethynylphenyl)-6,7-bis(2-methoxyethoxy)quinazolin-4-amine, nilotinib, which is a tyrosine kinase inhibitor and has the chemical structure 4-methyl-N-[3-(4-methyl-1H-imidazol-1-yl)-5-(trifluoromethyl)phenyl]-3-[(4-pyridin-3-ylpyrimidin-2-yl)amino]benzamide, and lapatinib, which inhibits the tyrosine kinase activity associated with the oncogenes EGFR and Her2/neu and has the chemical structure N-[3-chloro-4-[(3-fluorophenyl)methoxy]phenyl]-6-[5-[(2-methylsulfonylethylamino)methyl]-2-furyl]quinazolin-4-amine. Still other small molecule kinase inhibitors are known in the art, such as, but not limited to, the mTOR inhibitors, including rapamycin, FK506 (tacrolimus), and analogues and derivatives thereof.

Accordingly, compositions according to the present invention can comprise one or more of the biologically active components described above in any suitable combinations. Examples of combinations that can be incorporated in compositions according to the present invention include, but are not limited to: (1) a nucleic acid or a derivative thereof plus a peptide, protein, or a derivative of a peptide or protein; (2) a nucleoside, nucleotide, or a derivative of a nucleoside or nucleotide plus a peptide, protein, or a derivative of a peptide or protein; (3) a carbohydrate or a derivative thereof plus a lipid or derivative thereof; (4) a carbohydrate or derivative thereof plus a lipopeptide or derivative thereof; (5) a nucleic acid or a derivative thereof plus a metal ion; (6) a nucleoside, nucleotide, or a derivative of a nucleoside or nucleotide plus a metal ion; (7) a peptide, protein, or a derivative of a peptide or protein plus a metal ion; (8) a nucleic acid or a derivative thereof plus a thiol; (9) a nucleoside, nucleotide, or a derivative of a nucleoside or nucleotide plus a thiol; (10) a peptide, protein, or a derivative of a peptide or protein plus a thiol; (11) a nucleic acid or a derivative thereof plus an antibiotic or derivative thereof; (12) a nucleoside, nucleotide, or a derivative of a nucleoside or nucleotide plus an antibiotic or derivative thereof; (13) a peptide, protein, or a derivative of a peptide or protein plus an antibiotic or derivative thereof; (14) a nucleic acid or a derivative thereof plus a vitamin or derivative thereof; (15) a nucleoside, nucleotide, or a derivative of a nucleoside or nucleotide plus a vitamin or derivative thereof; (16) a peptide, protein, or a derivative of a peptide or protein plus a vitamin or derivative thereof; (17) a nucleic acid or a derivative thereof plus a bioflavonoid or derivative thereof; (18) a nucleoside, nucleotide, or a derivative of a nucleoside or nucleotide plus a bioflavonoid or derivative thereof; (19) a peptide, protein, or a derivative of a peptide or protein plus a bioflavonoid or derivative thereof; (20) a nucleic acid or a derivative thereof plus an antioxidant or derivative thereof; (21) a nucleoside, nucleotide, or a derivative of a nucleoside or nucleotide plus an antioxidant or derivative thereof; or (22) a peptide, protein, or a derivative of a peptide or protein plus an antioxidant or derivative thereof. Other combinations are possible, such as compositions comprising 3, 4, 5, 6, or up to 16 biologically active components. Various combinations including multiple biologically active components are described in Examples 6-10, below. Depending on the exact combination of components, multiple components can be added to the carrier in a single reaction; alternatively, multiple rounds of reaction can be used, with a single component or multiple components being added in each round of reaction. Examples of these combinations, with either multiple components being added in a single round of reaction or with multiple rounds of reactions, are described in Examples 6-10, below. In Example 6, the biologically active components are ofloxacin, curcumin, rutin, G1/9 peptide (CKRNIFKSY) (SEQ ID NO: 1), G2/4 peptide (CQIDKNKPKYYILDMFPYPSG) (SEQ ID NO: 2), and B3 peptide (CKPKDMVDNYPSTWRERRRKKR) (SEQ ID NO: 3). The first three components (ofloxacin, curcumin, and rutin) are added in a first round of reaction. The last three components (G1/9 peptide, G2/4 peptide, and B3 peptide) are added in a second round of reaction. In Example 7, the biologically active components are retinoic acid, rutin, G1/9 peptide, G2/4 peptide, and B3 peptide. The first two components (retinoic acid and rutin) are added in a first round of reaction. The last three components (G1/9 peptide, G2/4 peptide, and B3 peptide) are added in a second round of reaction. In Example 8, the biologically active components are LPS (lipopolysaccharide), PG (peptidoglycan), DNA, imiquimod, G1/9 peptide, G2/4 peptide, B3 peptide, novobiocin, glutathione, and tiamulin. The first four components (LPS, PG, DNA, and imiquimod) are added in a first round of reaction. The next three components (G1/9 peptide, G2/4 peptide, and B3 peptide) are added in a second round of reaction. The last three components (novobiocin, glutathione, and tiamulin) are added in a third round of reaction. In Example 9, the biologically active components are LPS (lipopolysaccharide), PG (peptidoglycan), DNA, imiquimod, G1/9 peptide, G2/4 peptide, B3 peptide, retinoic acid, and tiamulin. The first four components (LPS, PG, DNA, and imiquimod) are added in a first round of reaction. The next three components (G1/9 peptide, G2/4 peptide, and B3 peptide) are added in a second round of reaction. The last two components (retinoic acid and tiamulin) are added in a third round of reaction. In Example 10, the biologically active components are LPS (lipopolysaccharide), PG (peptidoglycan), DNA, imiquimod, G1/9 peptide, G2/4 peptide, B3 peptide, lactoferricin, and thymulin. The first four components (LPS, PG, DNA, and imiquimod) are added in a first round of reaction. The next three components (G1/9 peptide, G2/4 peptide, and B3 peptide) are added in a second round of reaction. The last two components (lactoferricin and thymulin) are added in a third round of reaction. In some cases, when multiple components are added in a single round of reaction, it may be preferred to add the components in a defined sequential order. For example, when G1/9 peptide, G2/4 peptide, and B3 peptide are added in a single round of reaction, it is preferred to add them in that order (first G1/9 peptide. then G2/4 peptide, and finally B3 peptide).

Accordingly, in general, a biologically active composition according to the present invention comprises:

(1) at least one of the following biologically active components:

(a) a nucleic acid or a derivative thereof;
(b) a nucleoside, nucleotide, or a derivative of a nucleoside or nucleotide;
(c) a peptide, protein, or a derivative of a peptide or protein;
(d) a lipopolysaccharide or a derivative thereof;
(e) a peptidoglycan or a derivative thereof;
(f) a carbohydrate or a derivative thereof;
(g) a lipid or a derivative thereof;
(h) a lipopeptide or a derivative thereof;
(i) a metal ion;
(j) a thiol;
(k) an antibiotic or a derivative thereof;
(l) a vitamin or a derivative thereof;
(m) a bioflavonoid or a derivative thereof;
(n) an antioxidant or a derivative thereof;
(o) an immune response modifier;
(p) an antibody;
(q) a biologically active nonmetal;
(r) histamine or an antihistamine; and
(s) a kinase inhibitor; and
(2) at least one carrier effective to deliver the composition to a phagocytic cell such that the biologically active component is taken up by the phagocytic cell and influences its biological activity.

In one alternative, the composition can comprise an immune active antigen or antigenic epitope. The immune active antigen or antigenic epitope can be, but is not limited to, a peptide, a protein, a recombinant peptide or multi-peptide, or a recombinant protein. When the composition comprises an immune active antigenic epitope, the composition can elicit a protective immune response in vivo.

In another alternative, the composition can comprise double-stranded RNA, siRNA, pre-miRNA, miRNA, poly U or GU-rich nucleotide sequences.

In the compositions, the molecules can be present as a mixture. Alternatively, the molecules can be chemically linked together; in this alternative, the at least one biologically active component is linked to the carrier. The carrier is typically a microparticle. Preferably, the microparticles have a narrow size distribution range. The microparticles can be porous or non-porous. Typically, the microparticles are less than about 10 μm in diameter; more typically, the microparticles are less than about 5 μm in diameter. Typically, the microparticles are made of a biopolymer. In one alternative, the components are non-covalently attached to the microparticles. In another alternative, the components are covalently attached to the microparticles. Typically, the microparticles are in the same size range as a pathogen. When the microparticles are in the same size range as a pathogen, the composition can comprise an immune active antigen antigenic epitope or immune modulator or modulators, and the immune active antigen or antigenic epitope can be a peptide, a protein, a recombinant peptide or multi-peptide, a recombinant protein, a lipid, a carbohydrate, or a combination of these. The composition can comprise both an immune active antigen or antigenic epitope and an immune modulator or modulators.

In one alternative, the at least one biologically active component is reversibly linked to the carrier. The at least one biologically active component can be reversibly linked to the carrier through disulfide linkages. Alternatively, the at least one biologically active component can be reversibly linked to the carrier through linkages comprising immobilized metal chelates. The immobilized metal chelates can comprise chelates of zinc, copper, iron, or other metals. In another alternative, the reversible linkages can be ionic or hydrophobic linkages.

Another aspect of the present invention is a method of eliciting an biological response in a cell culture, cell subset, or a multicellular organism such as a plant, an animal, or a human subject comprising the step of administering an amount of a composition comprising the selected biologically active component associated with microparticles, wherein the microparticles are smaller than or in the same size range as a pathogen. The amount administered is sufficient to elicit an immune response in the cell culture, the cell subset, or the multicellular organism subject. When the method is a method of eliciting a biological response in a cell subset, the composition can be administered in a cell culture.

According to the present invention, administration of the composition can be performed in a cell culture or via a mucosal route, a parenteral route, or a dermal route into an multicellular host, such as a plant, an animal, or a human. Other routes of administration could alternatively be used.

Toxicity and efficacy of compositions according to the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. The data obtained from these cell culture assays and animal studies can be used in formulating a range of dosage for use in humans or in other animals. The dosage of such compositions lies preferably within a range of circulating concentrations that include the $ED_{50}$ with little or no toxicity. The dosage may vary within this range depending upon the dosage form employed and the route of administration utilized.

Another aspect of the present invention is a method for studying the effect of acute infections on the pathogenesis of a condition selected from the group consisting of: (i) a chronic inflammatory disease selected from the group consisting of allergies, asthma, and autoimmune conditions; and (ii) a malignant condition selected from the group consisting of cancer and tumor metastasis, comprising the steps of:

(1) providing an animal model susceptible to a condition selected from the group consisting of: (i) a chronic inflammatory disease selected from the group consisting of allergies, asthma, and autoimmune conditions; and (ii) a malignant condition selected from the group consisting of cancer and tumor metastasis;

(2) administering a composition according to the present invention, wherein, in the composition, the microparticles are in the same size range as a pathogen, wherein the composition comprises an immune active antigen or antigenic epitope, and wherein the immune active antigen or antigenic epitope is a peptide, a protein, a recombinant peptide or multi-peptide, or a recombinant protein, to the animal model to treat or prevent an infection in the animal model through an immune response resulting from the administration of the composition; and (3) determining the effect of the composition administered in step (2) on the condition selected from the group consisting of: (i) a chronic inflammatory disease selected from the group consisting of allergies, asthma, and autoimmune conditions; and (ii) a malignant condition selected from the group consisting of cancer and tumor metastasis.

The invention is illustrated by the following Examples. These Examples are included for illustrative purposes only, and are not intended to limit the invention.

Example 1

Selection of Microparticles

Agarose microparticles in the 1-10 μm ranges have been produced by Sterogene Bioseparations, Inc. (Carlsbad, Calif.) and tested using a Saturn DigiSizer 5200 (Micromeritis Instrument Corp). The results showed that the particle distribution is 75% is below 5 μm, 24% is 5-10 μm and 1% is above 10 μm.

Example 2

Activated Agarose Microparticles

Particles were activated by two different methods. The activation methods were performed by Sterogene Bioseparations, Inc. (Carlsbad, Calif.), using a thiol-disulfide ligand exchange chemistry. In this linkage chemistry, which provides for a reversible covalent attachment of ligands the microparticles were functionalized with a high density of thiol groups. The peptides and the other biomolecules were either functionalized with 2-thiopyridyl moieties or epoxide groups. The 2-thiopyridyl functionalized peptides would get released from the microparticles after cellular internalization due to the strong intracellular reducing milieu. Another advantage of this chemistry is the highly effective and reproducible immobilization of ligands.

Another method of immobilization was performed by using a immobilized metal chelation (IMAC) chemistry. The agarose microparticles were functionalized with $Zn^{2+}$ ions according to standard methods. The peptides of choice as well as other biologically active compounds contain chelating moieties (e.g., lysine, cysteine, tryptophan, heterocyclic ring structures, amide bonds, sulfur containing residues, etc.) that can readily chelate the immobilized $Zn^{2+}$ ions.

Example 3

Bioinformatics analysis of antigenic proteins of pathogens can also lead to the identification of peptide epitopes of high antigenic potentials. Such analysis has been performed for the *M. gallisepticum* MGA protein. The antigenic regions were further analyzed in the context of linear antigenic motifs.

Example 4

Preparation of MG Peptide Immune Modulator on the Thiol Functionalized Microparticles Preparation of an immune modulatory composition: To 2.5 ml thiol functionalized microparticles (Sterogene Bioseparations, Inc., Carlsbad, Calif.), a mixture of epoxylated 50 μg LPS, 50 μg peptidoglycan (PG), and 250 μg *E. coli* DNA was added. After 4 h agitation, the slurry was centrifuged and washed once with LAL water. Then 125 μg of thiolated poly-I:C was added and continued to couple for 4 h. Subsequently, it was centrifuged, washed 3 times with LAL water and 0.125 mg 2-cys-thiopyridyl B3 peptide was added and continued to couple for 4 h. Then, the mixture was once washed with LAL water and 0.125 mg single MHC I and MHC II peptide epitope mixture (G1/9+G2/4) containing the N terminal 2-cys-thiopyridyl moiety was added and continued to couple for 4 h. (These peptides contain an N terminal 2-thiopyridyl reactive group for coupling to the thiol particles). The coupling efficiencies were measured by $OD_{343}$ in the supernatants. After washing with LAL water, the particles were resuspended in an equal volume of LAL water.

In another coupling reaction, the Zn-chelating microparticles were used at the same peptide and agonist concentrations as follows: To 2 ml Zn-chelating microparticles (Sterogene Bioseparations, Inc., Carlsbad, Calif.), the mixture of 40 μg LPS, 40 μg PG, 100 μg poly-1:C and 200 μg DNA were added and gently rocked for 3 h. The mixture was centrifuged, and washed twice with 6 ml LAL water. Subsequently, 60 μg G119, 60 μg G2/4 and 60 μg B3 peptides were added in this order (in 2 ml final volume) with gentle manual mixing after each addition. After 12 h of gentle rocking, the suspension was centrifuged and washed three times with 6 ml LAL water. The particles were resuspended in an equal volume of LAL water.

Example 5

Immobilization of Other Biologically Active Molecules

We have immobilized the following additional agonists to the Zn chelating microparticles: kinase inhibitors like curcumin and rutin, lactoferrin, lactoferricin, glutathione and N-acetylcysteine for improving intracellular redox potential, thymulin, antibiotics (e.g., ofloxacin and tiamulin), selenium, imiquimod, polybasic peptides like poly-lysine, antimicrobial basic peptides, proline-rich peptides, antioxidants and vitamins.

Example 6

To 2 ml Zn chelating microparticles, add first 0.5 mg ofloxacin, 0.5 mg curcumin, and 0.5 mg rutin, and gently rock for 1 h. Centrifuge, save supernatant and wash once with 6 ml LAL water and pool. Wash once more and discard wash. Subsequently add 20 μg G1/9, 20 μg G2/4 and 20 μg B3 peptides in this order (2 ml volume) with gentle manual mixing after each additions. After 1 h gentle rocking, centrifuge and save supernatant. Wash once with 6 ml LAL water and pool with supernatant. Repeat wash two more times each. Resuspend in equal volume of LAL water and then separate into two vials of equal volume. Coupling efficiency from the supernatant and first wash mixture was determined.

Example 7

To 2 ml Zn chelating microparticles add first 0.5 mg retinoic acid and 0.5 mg rutin, and gently rock for 1 h. Centrifuge, save supernatant and wash once with 6 ml LAL water and pool. Wash once more and discard wash. Subsequently add 20 μg G1/9, 20 μg G2/4 and 20 μg B3 peptides in this order (2 ml volume) with gentle manual mixing after each addition. After 1 h gentle rocking, centrifuge and save supernatant. Wash once with 6 ml LAL water and pool with supernatant. Repeat wash two more times each. Resuspend in equal volume of LAL water and then separate into two vials of equal volume. Coupling efficiency from the supernatant and first wash mixture was determined.

Example 8

To 2 ml Zn chelating microparticles add the mixture of 40 μg LPS, 40 μg PG, 200 μg DNA, and 10 μg imiquimod, and gently rock for 1 h. Subsequently add 20 μg G119, 20 μg G2/4 and 20 μg B3 peptides in this order (2 ml volume) with gentle manual mixing after each additions. After 1 h gentle rocking, centrifuge and save supernatant. Wash once with 6 ml LAL water and pool with supernatant. Then add 0.5 mg novobiocin, 0.5 mg glutathione, and 0.5 mg tiamulin. After 3 h gentle rocking, centrifuge and save supernatant. Wash once with 6 ml LAL water and pool with supernatant. Repeat wash two more times each. Resuspend in equal volume of LAL water and then separate into two vials of equal volume. Coupling efficiency from the supernatant and first wash mixture was determined.

Example 9

To 2 ml Zn chelating microparticles add the mixture of 40 μg LPS, 40 μg PG, 200 μg DNA, and 10 μg imiquimod, and gently rock for 1 h. Subsequently add 20 μg G1/9, 20 μg G2/4 and 20 μg B3 peptides in this order (2 ml volume) with gentle manual mixing after each addition. After 1 h gentle rocking, centrifuge and save supernatant. Wash once with 6 ml LAL water and pool with super. Then add 0.5 mg retinoic acid and 0.5 mg tiamulin. After 3 h gentle rocking, centrifuge and save supernatant. Wash once with 6 ml LAL water and pool with supernatant. Repeat wash two more times each. Resuspend in equal volume of LAL water and then separate into two vials of equal volume. Coupling efficiency from the supernatant and first wash mixture was determined.

Example 10

To 2 ml Zn chelating microparticles add the mixture of 40 μg LPS, 40 μg PG, 200 μg DNA, and 10 μg imiquimod, and gently rock for 1 h. Subsequently add 20 μg G1/9, 20 μg G2/4 and 20 μg B3 peptides in this order (2 ml volume) with gentle manual mixing after each addition. After 1 h gentle rocking, centrifuge and save supernatant. Wash once with 6 ml LAL water and pool with supernatant. Then add 50 μg lactoferricin and 50 μg thymulin. After 3 h gentle rocking, centrifuge and save supernatant. Wash once with 6 ml LAL water and pool with supernatant. Repeat wash two more times each. Resuspend in equal volume of LAL water and then separate into two vials of equal volume. Coupling efficiency from the supernatant and first wash mixture was determined.

Example 11

Animal Studies

The immune modulatory compositions were administered orally into three-day-old chicks (free of $M.$ $gallisepticum$ (MG) and $M.$ $synoviae$ (MS) with no MG and MS maternal antibodies detected by ELISA). In each group, there were 10 chickens. The chicken's individual body weights were recorded. The chickens were allocated such that their average body weight in each group would not be statistically different. Each bird was identified by colored and numbered wing tags according to the treatment and their body weight recorded on the appropriate form. At 14 days of the experiment, chickens were challenged with $M.$ $gallisepticum$ $R_{low}$ strain. The study was terminated at 28 days.

The groups were set up as follows: G1 and G2 were negative and positive controls. G1 non-challenged and non-treated G2=challenged and non-treated. G3=treated orally with thiol-based functionalized microparticles (0.2 ml/chicken) and challenged. G4=treated orally with Zn chelate-based functionalized microparticles (0.2 ml/chicken) and challenged.

Timeline

Day −1: Setting-up of groups G1-G4. Sacrificed 10 chickens for ELISA assay, PCR and culturing of $M.$ $gallisepticum$ and $M.$ $synoviae$ to confirm that the experimental chickens are negative for maternal antibodies and the presence of $M.$ $gallisepticum$ and $M.$ $synoviae$.

Day 0: Oral vaccination of G3-G4 prior to challenge by using 0.2 ml of the microparticle compositions.

Day 14: Challenge of groups G2-G4. The animals were challenged using a fresh broth culture of the virulent R-strain of $M.$ $gallisepticum$, at a titer of about $8.0$ $\log_{10}$ CFU/ml. Ten ml of this fresh broth culture was administered to each of these groups using a spray technique. Briefly, the birds were placed in an isolation unit. Fresh $M.$ $gallisepticum$ R-strain culture ($10^7$ particles/ml) was then sprayed into the isolation unit and the chickens left exposed for 20 minutes.

Days D14 and D28: Chickens were bled in order to obtain serum to be tested for MG-specific antibodies using a serum plate agglutination (SPA) test and blocking ELISA.

Day 28: G1-G4. Euthanasia, necropsy, and plating for the isolation of $M.$ $gallisepticum$ (MG) from specified organs, trachea, air sac and lung. Histological examinations of trachea and lung were performed.

Euthanasia and Pathology

On D28, at the end of the experimental study, all groups were euthanized. Each bird was necropsied and scored for gross lesions associated with MG. The presence of exudate in the trachea, left and right thoracic air sacs and peritoneum were recorded. The lesions were scored according to the following system: In trachea: 0=no exudates, 1=slight redness and small quantity of exudates, 2=redness of mucous membrane, exudates. Left and right air sacs: 0=no lesion, 1=serous exudates, 2=serous exudates with small pieces of fibrin, 3=serous, fibrinous exudates, slightly thickened air sac wall, 4=lots of fibrinous exudates, very thickened air sac wall. Peritoneum: 0=no exudates, 1=serous exudates, 2=serous exudate with small pieces of fibrin, 3=serous-fibrinous exudates.

MG Reisolation

During necropsy examination, trachea, thoracic air sacs, liver, lung, spleen, kidney and heart were aseptically sampled using swabs. Materials from the swabs were then plated onto mycoplasma agar (MA) and incubated at 37° C. in a 5% $CO_2$ incubator. Plates were observed for mycoplasma on days 2, 4, and 7, and then at weekly intervals for a maximum of three weeks. Positive colonies were tested by PCR to identify $M.$ $gallisepticum$ and $M.$ $synoviae$.

Necropsy

Subsequent to MG challenge, significant pathological lesions were recognized in the air-sac and the peritoneum. However, significant reduction in lesion scores was recorded in the groups treated with particles containing immune active peptides plus agonists (G3, G4 p<0.001), in comparison with the control (G2) non-treated, challenged group.

Re-Isolation of $Mycoplasma$ $Mycoplasma$ can be frequently re-isolated from the inner organs of the non-treated, infected control chickens. Complete elimination of mycoplasma (from respiratory+inner organs) was noticed in groups treated with the functionalized microparticles (G3, G4) in comparison to the non-treated control (G2) group. Similar results were obtained when the re-isolation rate of mycoplasma from respiratory tract (trachea, lung, air-sac) or from other inner organs (liver, spleen, kidney and heart) of the experimental groups were compared.

The results are shown in Table 1.

TABLE 1

| Groups | Necropsy results Percentage of lesion scores | Effi-ciency | Percentage of M. gallisepticum reisolation from inner organs | Effi-ciency |
|---|---|---|---|---|
| G1-negative control | 0% | N/A | 0% | N/A |
| G2-positive control | 78% | 53.2% | 23% | 0% |
| G3-thiol particles + 10 µg epitope peptide + agonists | 5% | 95% | 0% | 100% |
| G4-Zn particles + 10 µg epitope peptide + agonists | 6% | 94% | 0% | 100% |

Serological Results

Serological response of the groups was different at the end of the experiment. The reaction of the non-treated, challenged group (G2) was low. At the same time, significantly stronger reaction was noticed in the group treated with particles plus peptide epitopes and agonists (G 3,4) (p<0.05).

Discussion

*M. gallisepticum* can cause significant inflammation in the air-sac and peritoneum which is accompanied by colonization of trachea, air-sac and the lungs. *Mycoplasma* can also be detected frequently from inner organs. We have developed a new type of "pathogen mimicking" immunologically active compositions consisting of microparticles in the size range of microorganisms (<5 µm), having antigenic epitope peptides or other antigens immobilized along with different agonist immunomodulatory molecules.

Our results showed that when antigenic molecules were added to the particles coated with selected immunomodulatory compounds, mycoplasma-specific serological response was enhanced. The colonization of organs was reduced to an insignificant level and scores of pathological lesions was low. This effect was more observed when the microparticles were introduced mucosally and before challenge.

After administration of the compositions and prior to challenge, the treated chickens were examined daily to evaluate the safety of the composition. The chickens were found to be clinically healthy, and showed no side effects. The animals necropsied during the course of the study showed no signs of inflammation or change in organ size/weight. The compositions appear to be safe. Besides prevention, these compositions can be used to treat a clinically established infection. This is significant because of the link existing between chronic inflammatory conditions such as infections, allergy, autoimmunity and cancer.

ADVANTAGES OF THE INVENTION

The present invention provides improved compositions and methods for the controlled dosage introduction of multiple biologically active molecules into phagocytic cells. These compositions are stable and can be prepared in a wide range of concentrations in order to bring about the desired biological effect. An example of such effect is an immune response. They are suitable for both in vitro and in vivo administration by a variety of routes. Their structure prevents premature breakdown or release of the effector molecules in vivo. The particles have intrinsic muco-adhesive properties that can improve their interaction with mucosal membranes and facilitate uptake.

Compositions according to the present invention have industrial applicability for the delivery of biologically active components to cells, especially phagocytic cells, in order to affect the functions of other cell types through their interactions with phagocytic cells.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of skill in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. A composition wherein the composition consists essentially of:
   (1) an alternative selected from the group consisting of: (a) LPS (lipopolysaccharide), PG (peptidoglycan), DNA, imiquimod, G1/9 peptide, G2/4 peptide, B3 peptide, novobiocin, glutathione, and tiamulin; (b) LPS (lipopolysaccharide), PG (peptidoglycan), DNA, imiquimod, G1/9 peptide, G2/4 peptide, B3 peptide, lactoferricin, and thymulin; and (c) LPS (lipopolysaccharide), PG (peptidoglycan), DNA, imiquimod, G1/9 peptide, G2/4 peptide, B3 peptide, lactoferricin, and thymulin; and
   (2) a non-crosslinked polysaccharide biopolymer carrier effective to deliver the composition to a phagocytic cell such that the biologically active components are taken up by the phagocytic cell and influences its biological activity by the specific activity associated with the biologically active component, wherein each of the biologically active components is covalently linked to the polysaccharide biopolymer carrier, wherein the non-crosslinked polysaccharide biopolymer carrier is agarose.

2. The composition of claim 1 wherein the composition comprises an immune active antigen or antigenic epitope.

3. The composition of claim 2 wherein the composition elicits a protective immune response in vivo.

4. The composition of claim 1 wherein the carrier is an agarose microparticle.

5. The composition of claim 4 wherein the agarose microparticle has a narrow size distribution range.

6. The composition of claim 4 wherein the agarose microparticle is porous.

7. The composition of claim 4 wherein the agarose microparticle is less than about 10 μm in diameter.

8. The composition of claim 4 wherein the agarose microparticle is less than about 5 μm in diameter.

9. The composition of claim 4 wherein the agarose microparticle is in the same size range as a pathogen.

10. The composition of claim 1 wherein the at least one biologically active component is reversibly linked to the carrier.

11. The composition of claim 10 wherein the at least one biologically active component is reversibly linked to the carrier through disulfide linkages.

* * * * *